(12) United States Patent
Reddy et al.

(10) Patent No.: US 11,002,524 B2
(45) Date of Patent: May 11, 2021

(54) CYCLIC COMPOUNDS AND PROCESS FOR THE PREPARATION THEREOF

(71) Applicant: Council of Scientific & Industrial Research, New Delhi (IN)

(72) Inventors: Dumbala Srinivasa Reddy, Pune (IN); Rahul Dilip Shingare, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 234 days.

(21) Appl. No.: 16/088,871

(22) PCT Filed: Mar. 30, 2017

(86) PCT No.: PCT/IN2017/050117
§ 371 (c)(1),
(2) Date: Sep. 27, 2018

(87) PCT Pub. No.: WO2017/168447
PCT Pub. Date: Oct. 5, 2017

(65) Prior Publication Data

US 2019/0242686 A1     Aug. 8, 2019
US 2020/0249002 A9     Aug. 6, 2020

(30) Foreign Application Priority Data

Mar. 30, 2016 (IN) .............................. 201611011069

(51) Int. Cl.
| | |
|---|---|
| *G01B 3/1003* | (2020.01) |
| *C09D 177/06* | (2006.01) |
| *G01B 1/00* | (2006.01) |
| *G01B 3/1005* | (2020.01) |
| *G01B 3/1041* | (2020.01) |
| *G01B 3/1056* | (2020.01) |
| *G01B 3/1071* | (2020.01) |
| *C07D 471/06* | (2006.01) |
| *C07D 241/44* | (2006.01) |

(52) U.S. Cl.
CPC ......... *G01B 3/1003* (2020.01); *C07D 241/44* (2013.01); *C07D 471/06* (2013.01); *C09D 177/06* (2013.01); *G01B 1/00* (2013.01); *G01B 3/1005* (2013.01); *G01B 3/1041* (2013.01); *G01B 3/1056* (2013.01); *G01B 3/1071* (2013.01); *G01B 2003/103* (2013.01); *G01B 2003/1053* (2013.01); *G01B 2003/1076* (2013.01)

(58) Field of Classification Search
CPC ...... G01B 3/1003; G01B 1/00; G01B 3/1005; G01B 3/1041; G01B 3/1056; G01B 3/1071; C07D 241/44; C07D 471/06
USPC ........................................................ 514/80
See application file for complete search history.

(56) References Cited

U.S. PATENT DOCUMENTS 9,822,113 B2 * 11/2017 Reddy .................... A61P 31/04

FOREIGN PATENT DOCUMENTS

WO     2015004687     1/2015

OTHER PUBLICATIONS

Saito et al Biochemistry, 1967, 6(11) 3602-3608 (Year: 1967).*
Saito et al., "Chemical Studies on Riboflavin and Related Compounds. I. Oxidation of Quinoxaline-2,3-diols as a Possible Model for the Biological Decomposition of Riboflavin", Biochemistry, vol. 6, No. 11, 1967, pp. 3602-3608.

(Continued)

*Primary Examiner* — Yevgeny Valenrod
(74) *Attorney, Agent, or Firm* — Dinsmore & Shohl, LLP

(57) ABSTRACT

The present invention discloses a cyclic compound of formula (I) and a process of preparation thereof. The present invention further discloses a process for the preparation of compound of formula (II) preferably Hunanamycin A from compound of formula (I).

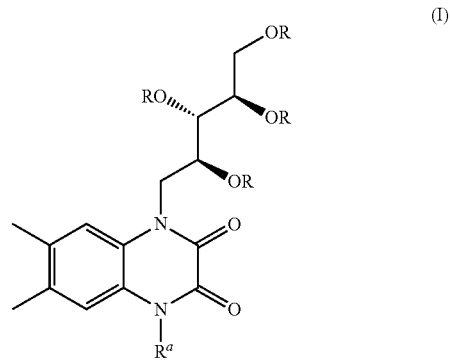

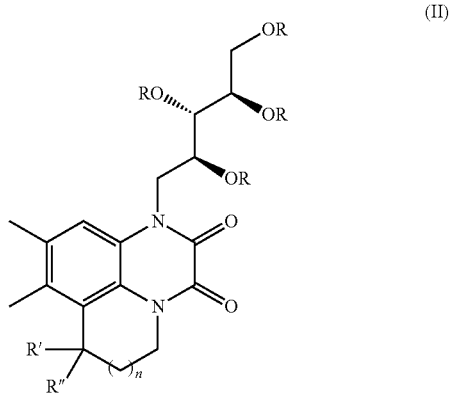

12 Claims, No Drawings

(56) References Cited

OTHER PUBLICATIONS

Harkness et al., Bacterial Degradation of Riboflavin: VI. Enzymatic Conversion of Riboflavin to 1-Ribityl-2,3-Diketo-1,2,3,4-Tetrahydro-6,7-Dimethylquinoxaline, Urea, and Carbon Dioxide, The Journal of Biological Chemistry, vol. 240, No. 10, 1965, pp. 4089-4096.
Harkness et al., "Bacterial Degradation of Riboflavin: V. Stoichiometry of Riboflavin Degradation to Oxamide and Other Products, Oxidation of C14-Labeled Intermediates and Isolation of the Pseudomonad Effecting These Transformations", Archives of Biochemistry and Biophysics, Academic Press, US, vol. 108, No. 2, 1964, pp. 323-333.
Thakuria et al., "One-pot efficient green synthesis of 1,4-dihydro-quinoxaline-2,3-dione derivatives", Journal of Chemical Sciences, vol. 118, No. 5, 2006, pp. 425-428.
Hu et al., "Hunanamycin A, an Antibiotic from a Marine-Derived Bacillus Hunanensis", Organic Letters, vol. 15, No. 2, 2013, pp. 390-393.
Shingare et al., "First Total Synthesis of Hunanamycin A", vol. 15, No. 17, 2013, pp. 4556-4559.
International Search Report and Written Opinion, completed Jul. 19, 2017, pertaining to PCT/IN2017/050117, Re-Issued Version.

\* cited by examiner

CYCLIC COMPOUNDS AND PROCESS FOR THE PREPARATION THEREOF

FIELD OF THE INVENTION

The present invention relates to a cyclic compound of formula (I)

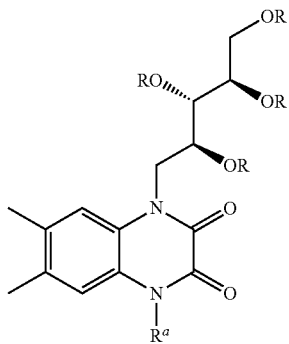

and a process of preparation thereof. The present invention further relates to a process for the preparation of compound of formula (II)

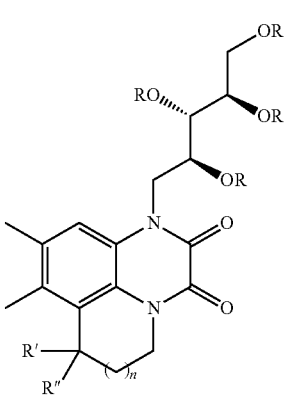

preferably Hunanamycin A from compound of formula (I).

BACKGROUND AND PRIOR ART OF THE INVENTION

Today, infectious diseases are the second major cause of death worldwide and the third leading cause of death in developed countries. In the US; bacteria are the most common cause of infection-related death. Bacteria of the genus *Salmonella* are a major cause of foodborne illness throughout the world. According to very recent WHO report, the global burden of foodborne diseases shows that almost 420,000 people die every year by eating contaminated food. The same also estimated that the African and South-East Asia Regions have the highest burden of foodborne diseases. As a zoonotic pathogen, *Salmonella* can be found in the intestines of many food-producing animals such as poultry and pigs. Infection is usually acquired by consumption of contaminated water or food of animal origin: mainly undercooked meat, poultry, eggs and milk. Most *Salmonella* strains cause gastroenteritis, while some strains, particularly *Salmonella enterica* serotypes Typhi and Paratyphi, are more invasive and typically cause enteric fever. Enteric fever is a more serious infection that poses problems for treatment due to ABR (Antibacterial resistance) in many parts of the world. For instance, in *Salmonella enterica* serotype Typhimurium, the genomic element that carries resistance to five antimicrobials (ampicillin, chloramphenicol, streptomycin, sulfonamides and tetracycline) may spread horizontally among other serotypes and acquire additional resistance determinants. In addition, bacteria often resilient enough to survive in even the extreme environments through evolution of different mechanisms. Hence, there is an urgent need for novel antibacterials to address resistance with novel mechanisms.

Hunanamycin A is the first natural product with a pyrido [1,2,3-de]quinoxaline-2,3-dione core and was isolated from a marine-derived *Bacillus hunanensis*. Hunanamycin A is the first natural product with a pyrido [1,2,3-de]quinoxaline-2,3-dione core related to a degradation product of riboflavin (vitamin-B2).

WO2015004687 disclosed novel tricyclic compounds of formula (I) and (II) More particularly, the present invention relates to novel tricyclic compounds of formula (I) and (II) and process of preparation of these compounds from 4,5-dimethyl-o-phenylinediamine. Further, the present invention relates to a process for preparation of tricyclic compound hunanamycin A.

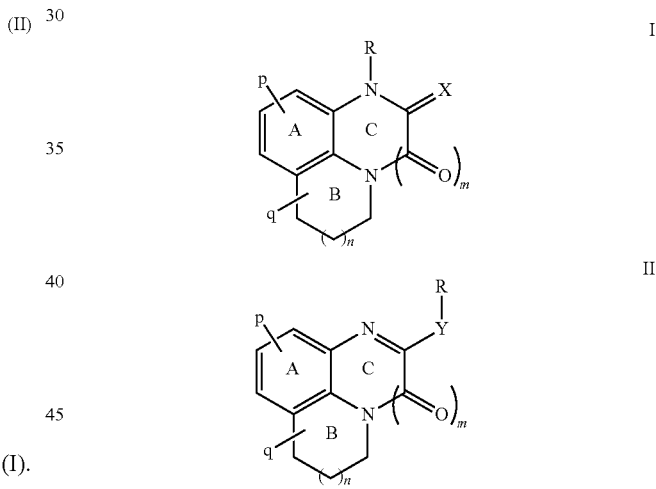

Article titled "Hunanamycin A, an Antibiotic from a Marine-Derived Bacillus hunanensis" by Youcai Hu et al. published in *Organic Letters*, 2013, Vol. 15, No. 2, 390-393 reports Hunanamycin A, the first natural product with a pyrido[1,2,3-de]quinoxaline-2,3-dione core, was isolated from a marine-derived Bacillus hunanensis. Hunanamycin A is related to a degradation product of riboflavin but has undergone an N-prenylation and subsequent cyclization.

Article titled "First total synthesis of Hunanamycin A" by Rahul D. Shingare et al. published in *Organic Letter*, 2013, 15 (17), pp 4556-4559 reports the first synthesis of an antibacterial natural product, hunanamycin A and analogues with variation at the sugar moiety, using simple and scalable chemistry.

Article titled "One-pot efficient green synthesis of 1,4-dihydro-quinoxaline-2,3-dione derivatives" by Harjyoti Thakuria et al. published in *Journal of Chemical Sciences*, 2006, 118(5), pp 425-428 reports an efficient synthesis of the potential pharmacophore 1,4-dihydroquinoxaline-2,3-dione (1) has been achieved in a one-pot reaction at room temperature from substitutedo-phenylene diamine and oxalic acid under solvent-free conditions by a simple grinding method with unsurpassed atom economy. Thermal and powder X-ray diffraction analysis was carried out for some hydrated crystals.

The prior art process involve multistep reaction sequence involving protection of functional groups and less overall yield. Therefore, there is a need in the art to provide simple and economic synthetic route for hunanamycin A. Accordingly, the present invention provides a simple process for the preparation of hunanamycin A from cheap and easily available starting material i.e. Riboflavin. Further, the developed route involves only three steps, protecting group free synthesis and also amenable for synthesis of new analogues.

OBJECTS OF THE INVENTION

The main object of the present invention is to provide a novel cyclic compounds of formula (I). Another object of the present invention is to provide a process for the preparation of cyclic compounds formula (I) from cheap and easily available starting material i.e. Riboflavin.

Yet another objective of the present invention is to provide a process for the preparation of compound of formula (II) preferably Hunanamycin A from compound of formula (I).

Still another object of the present invention is to provide cyclic compounds of formula (I) for preventing or treating infection caused by the gram positive as well as gram negative bacteria.

Still yet another object of the present invention is to provide cyclic compounds of formula (II) for preventing or treating infection caused by the gram positive as well as gram negative bacteria.

Still yet another objective of the present invention is to provide gram scale biomimetic synthesis of Hunanamycin A using cheap starting material, no column purification in step economy fashion.

SUMMARY OF THE INVENTION

Accordingly, the present invention provides a cyclic compound of formula (I) or a pharmaceutically acceptable salt thereof;

Formula (I)

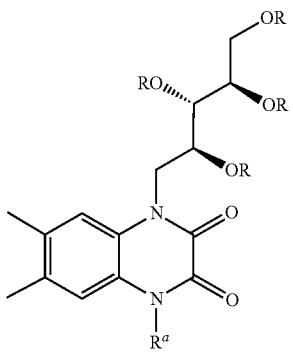

wherein R is selected from hydrogen, alkyl, aralkyl, alkoxyalkyl;

two R groups may be cyclized to form 5 or 6 membered ring which further substituted with alkyl groups or oxo group;

wherein $R^a$ is selected from hydrogen, sugar, sugar mimic, alkyl, aryl, aralkyl, alkenyl, alkynyl, haloalkyl, hydroxyalkyl, alkoxyalkyl, aminoalkyl, —$CH_2NR'R''$— CONR'R'',—COOR''';

wherein R', R'', R''' are independently hydrogen or alkyl, aryl, aralkyl which have additional substitution.

In an embodiment of the present invention, said compound is selected from group consisting of:

6,7-dimethyl-1-(3-methylbut-2-en-1-yl)-4-((2S,3S,4R)-2,3,4,5-tetrahydroxypentyl)-1,4-dihydroquinoxaline-2,3-dione (3);

1-allyl-6,7-dimethyl-4-((2S,3S,4R)-2,3,4,5-tetrahydroxypentyl)-1,4-dihydroquinoxaline-2,3-dione (4);

1-ethyl-6,7-dimethyl-4-((2S,3S,4R)-2,3,4,5-tetrahydroxypentyl)-1,4-dihydroquinoxaline-2,3-dione (5);

1-(2-cyclohexylideneethyl)-6,7-dimethyl-4-((2S,3S,4R)-2,3,4,5-tetrahydroxypentyl)-1,4-dihydroquinoxaline-2,3-dione (6);

ethyl 2-(6,7-dimethyl-2,3-dioxo-4-((2S,3S,4R)-2,3,4,5-tetrahydroxypentyl)-3,4-dihydroquinoxalin-1(2H)-yl) acetate (7);

1-benzyl-6,7-dimethyl-4-((2S,3S,4R)-2,3,4,5-tetrahydroxypentyl)-1,4-dihydroquinoxaline-2,3-dione (8);

1-isopentyl-6,7-dimethyl-4-((2S,3S,4R)-2,3,4,5-tetrahydroxypentyl)-1,4-dihydroquinoxaline-2,3-dione (9);

1-(2-cyclohexylethyl)-6,7-dimethyl-4-((2S,3S,4R)-2,3,4,5-tetrahydroxypentyl)-1,4-dihydroquinoxaline-2,3-dione (10).

In another embodiment of the present invention, a process comprising the steps of:

a) heating the basic solution of Riboflavin at temperature ranging from 80 to 90° C. for the time period ranging from 1 to 2 h followed by adding oxidizing agent and stirring resultant mixture at the temperature ranging from 25 to 30° C. for the time period ranging from 10 to 12 hrs to afford dione compound (2);

b) stirring the reaction mixture of compound of step (a), base and alkylating agent in solvent at the temperature ranging from 25 to 30° C. for the time period ranging from 10 to 12 hrs to obtain compound of formula (I).

In yet another embodiment of the present invention, said base in process step (b) is selected from the group consisting of sodium hydroxide, potassium hydroxide, potassium carbonate, cesium carbonate or sodium carbonate.

In an preferred embodiment of the present invention, said solvent in process step (b) is selected from the group consisting of dimethylformamide, N-methylpyrrolidine or dimethyl sulphoxide.

In still an embodiment of the present invention, said alkylating agent in process step (b) is selected from the group consisting of 3,3-Dimethylallyl bromide or 3,3-Dimethylallyl chloride.

In yet another embodiment of the present invention, said oxidizing agent in process step (a) is hydrogen peroxide.

In yet another embodiment of the present invention, a compound of Formula II or pharmaceutical acceptable salts are therefore

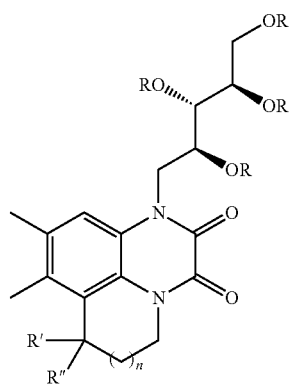

(II)

wherein R is selected from hydrogen, alkyl, aralkyl, alkoxyalkyl;

two R groups may be cyclized to form 5 or 6 membered ring which may further substituted with alkyl groups or oxo group;

wherein R', R", are independently hydrogen or alkyl, aryl, aralkyl which may have additional substitution;

n=0, 1, 2, 3

In still an embodiment of the present invention, a process for the conversion of said compound of formula (I) into Formula (II) comprising the steps of adding Lewis acid to a solution of compound of formula (I) in solvent at temperature ranging from 25 to 30° C. followed by stirring the reaction mixture at temperature ranging from 25 to 30° C. for the time period ranging from 5 to 6 hours to obtain compound of formula (II)

Formula (II)

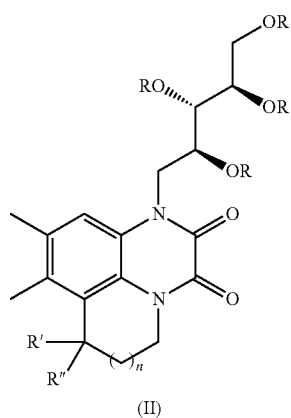

(II)

wherein R is selected from hydrogen, alkyl, aralkyl, alkoxyalkyl;

two R groups may be cyclized to form 5 or 6 membered ring which may further substituted with alkyl groups or oxo group;

wherein R', R", are independently hydrogen or alkyl, aryl, aralkyl which may have additional substitution;

n=0, 1, 2, 3

In still an embodiment of the present invention, said Lewis acid is selected from the group consisting of aluminium chloride ($AlCl_3$).

In another embodiment of the present invention, said compound of formula (II) is Hunanamycin A.

In yet another embodiment of the present invention, a pharmaceutical composition comprising novel cyclic compound of formula (I)

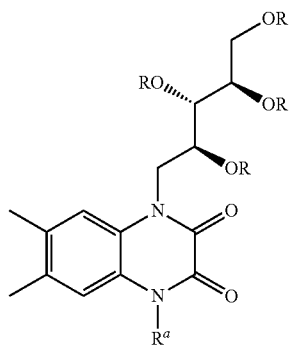

(I)

or formula (II)

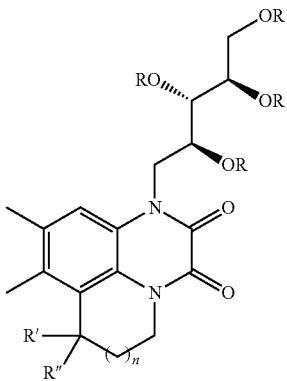

(II)

or a stereoisomer, or ester or pharmaceutically acceptable salt thereof and at least one pharmaceutically acceptable carrier.

In still another embodiment of the present invention, a method for preventing or treating bacterial infection caused by gram positive as well as gram negative bacteria in a subject in need thereof; comprising administering to the said subject a therapeutically effective amount of the compound of formula (I)

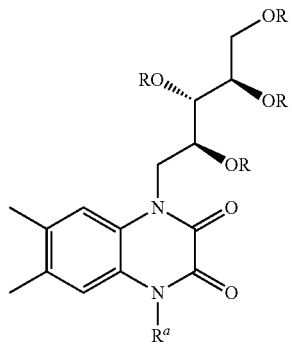

(I)

or formula (II)

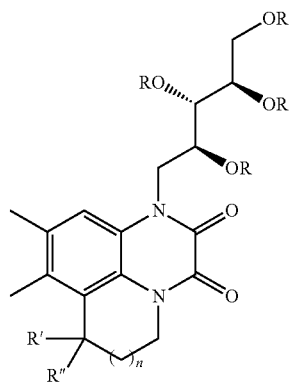

or a pharmaceutically acceptable salt thereof.

DETAILED DESCRIPTION OF THE INVENTION

The invention will now be described in detail in connection with certain preferred and optional embodiments, so that various aspects thereof may be more fully understood and appreciated.

In an embodiment, the present invention provides a novel cyclic compound of formula (I);

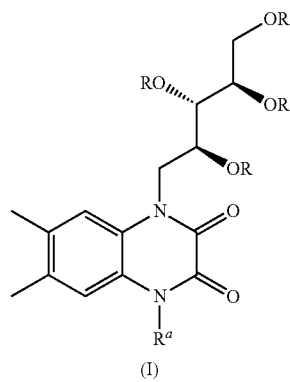

Formula (I)

wherein R is selected from hydrogen, alkyl, aralkyl, alkoxyalkyl;

two R groups may be cyclized to form 5 or 6 membered ring which may further substituted with alkyl groups or oxo group;

wherein $R^a$ is selected from hydrogen, sugar, sugar mimic, alkyl, aryl, aralkyl, alkenyl, alkynyl, haloalkyl, hydroxyalkyl, alkoxyalkyl, aminoalkyl, —CH$_2$NR'R"— CONR'R",—COOR'";

wherein R', R", R'" are independently hydrogen or alkyl, aryl, aralkyl which may have additional substitution.

In a preferred embodiment, said compound of formula (I) is selected from 6,7-dimethyl-1-(3-methylbut-2-en-1-yl)-4-((2S,3S,4R)-2,3,4,5-tetrahydroxypentyl)-1,4-dihydroquinoxaline-2,3-dione (3), 1-allyl-6,7-dimethyl-4-((2S,3S,4R)-2,3,4,5-tetrahydroxypentyl)-1,4-dihydroquinoxaline-2,3-dione (4), 1-ethyl-6,7-dimethyl-4-((2S,3S,4R)-2,3,4,5-tetrahydroxypentyl)-1,4-dihydroquinoxaline-2,3-dione (5), 1-(2-cyclohexylideneethyl)-6,7-dimethyl-4-((2S,3S,4R)-2,3,4,5-tetrahydroxypentyl)-1,4-dihydroquinoxaline-2,3-dione (6), Ethyl2-(6,7-dimethyl-2,3-dioxo-4-((2S,3S,4R)-2,3,4,5-tetrahydroxypentyl)-3,4-dihydroquinoxalin-1(2H)-yl)acetate (7), 1-benzyl-6,7-dimethyl-4-((2S,3S,4R)-2,3,4,5-tetrahydroxypentyl)-1,4-dihydroquinoxaline-2,3-dione (8), 1-isopentyl-6,7-dimethyl-4-((2S,3S,4R)-2,3,4,5-tetrahydroxypentyl)-1,4-dihydroquinoxaline-2,3-dione (9), 1-(2-cyclohexylethyl)-6,7-dimethyl-4-((2S,3S,4R)-2,3,4,5-tetrahydroxypentyl)-1,4-dihydroquinoxaline-2,3-dione (10).

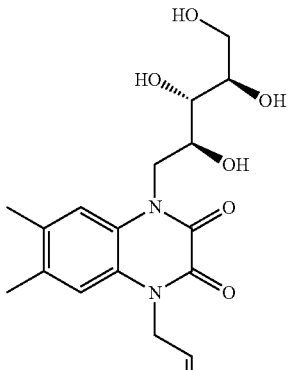

4

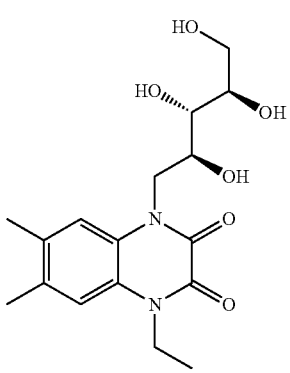

5

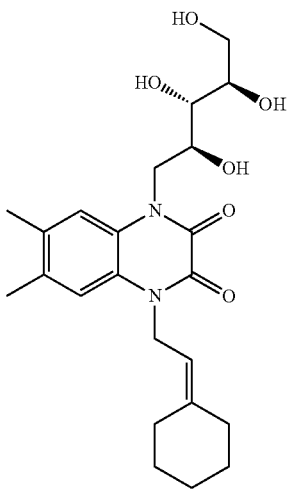

6

-continued

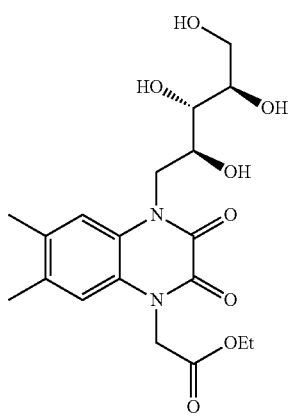
7

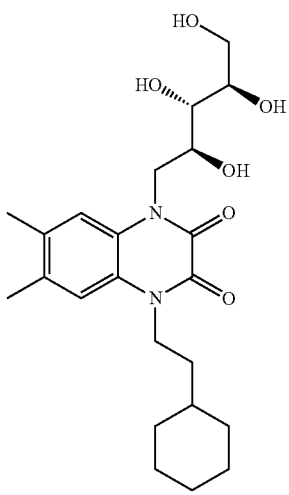
10

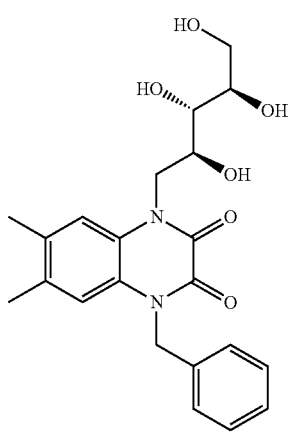
8

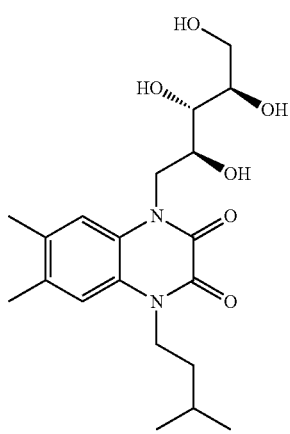
9

In an embodiment, the present invention provides a process for the preparation of compound of formula (I) from riboflavin or derivatives thereof, wherein said process comprising the steps of:

a) heating the basic solution of Riboflavin at temperature ranging from 80 to 90° C. for the time period ranging from 1 to 2 h followed by adding suitable oxidizing agent and stirring resultant mixture at the temperature ranging from 25 to 30° C. for the time period ranging from 10 to 12 hrs to afford dione compound (2);

b) stirring the reaction mixture of compound of step (a), base and suitable alkylating agent in solvent at the temperature ranging from 25 to 30° C. for the time period ranging from 10 to 12 hrs to afford compound of formula (I).

In preferred embodiment, said base in step (a) or (b) is selected from the group consisting of sodium hydroxide, potassium hydroxide, potassium carbonate, cesium carbonate or sodium carbonate.

In another preferred embodiment, said solvent of step (b) is selected from dimethylformamide (DMF), N-methylpyrrolidine and Dimethyl sulphoxide.

In yet another preferred embodiment, said alkylating agent in step (b) is selected from 3,3-Dimethylallyl bromide and 3,3-Dimethylallyl chloride.

In still another preferred embodiment, said oxidizing agent in step (a) is hydrogen peroxide.

In still another embodiment, the present invention provides use of compound of formula (I) for the process of preparation of compound of formula (II) preferably Hunanamycin A, wherein said process comprising the steps of adding Lewis acid to a solution of compound of formula (I) in solvent at temperature ranging from 25 to 30° C. followed by stirring the reaction mixture at temperature ranging from 25 to 30° C. for the time period ranging from 5 to 6 hours to afford compound of formula (II).

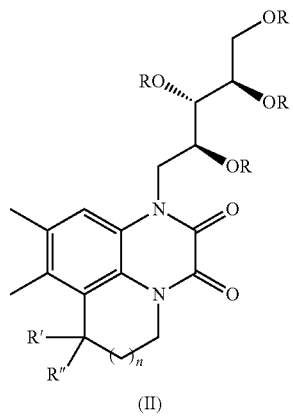

Formula (II)

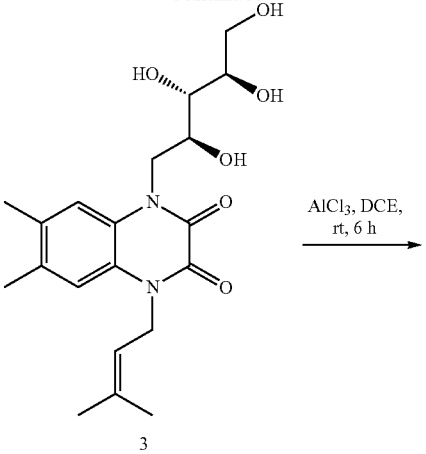

wherein R is selected from hydrogen, alkyl, aralkyl, alkoxyalkyl;

two R groups may be cyclized to form 5 or 6 membered ring which may further substituted with alkyl groups or oxo group;

wherein R', R", are independently hydrogen or alkyl, aryl, aralkyl which may have additional substitution;

n=0, 1, 2, 3

In preferred embodiment, said compound of formula (II) is Hunanamycin A.

In yet still another preferred embodiment, said lewis acid is such as aluminium chloride ($AlCl_3$).

The process for the preparation of Hunanamycin A from commercially available riboflavin is as shown in scheme 1 given below:

Scheme: 1

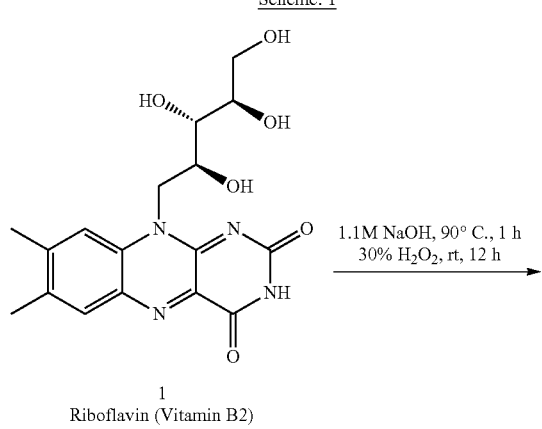

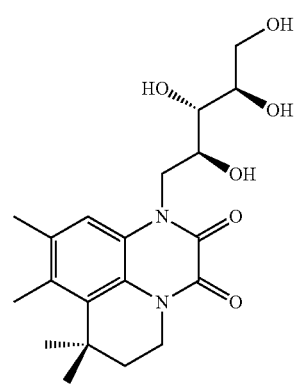

Hunanamycin A

In another embodiment, the present invention provides a pharmaceutical composition comprising novel cyclic compound of formula (I) or formula (II) or a stereoisomer, or ester or pharmaceutically acceptable salt thereof, and at least one pharmaceutically acceptable carrier, diluent or excipient.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, injections, gels and microspheres.

In another embodiment, the present invention relates to administering 'an effective amount' of the 'composition of invention' to the subject suffering from said disease. Accordingly, compound of formula (I) or (II) and pharmaceutical compositions containing them may be administered using any amount, any form of pharmaceutical composition via any route of administration effective for treating the disease. Typical routes of administering such pharmaceutical compositions include, without limitation, oral, topical, transdermal, inhalation, parenteral, sublingual, buccal, rectal, vaginal, and intranasal.

The pharmaceutical compositions of the invention are formulated so as to allow the active ingredients contained therein to be bioavailable upon administration of the composition to a patient. Compositions that will be administered to a subject or patient may take the form of one or more dosage units. The dosage forms can also be prepared as sustained, controlled, modified and immediate dosage forms.

In one embodiment, the present invention provides a method for preventing or treating bacterial infection caused by gram positive as well as gram negative bacteria, wherein said method comprises administering to the subject a therapeutically effective amount of cyclic compound of formula (I) or a stereoisomer, or ester or pharmaceutically acceptable salt thereof.

In another embodiment, the present invention provides a method for preventing or treating bacterial infection caused by gram positive as well as gram negative bacteria, wherein said method comprises administering to the subject a therapeutically effective amount of cyclic compound of formula (II) or a stereoisomer, or ester or pharmaceutically acceptable salt thereof.

The minimum inhibitory concentrations (MICs) are determined using the Promega Bac Titer-Glo microbial cell viability assay, which measures cell viability by quantitation of ATP present, an indicator of metabolic activity of cells. The assays are carried out using *Salmonella enterica* strain AMC (ATCC #6539), Inocula of *S. enterica* are prepared from 12-h broth cultures grown in Mueller Hinton broth and the suspensions were then adjusted to a turbidity of 0.5 McFarland. Assays are conducted in a 96-well plate using growth media with an inoculum of ~$5\times10^4$ CFU/mL using the suggested protocols. Bacterial cells are treated with hunanamycin analogs for 24 hours at ranges from 0.4 to 40 μg/mL and ciprofloxacin as a control ranging from 0.03 to 10 μg/mL. The $OD_{600}$ is measured using an Envision multimodal plate reader (Perkin-Elmer, Inc.). Following table 1 shows AntiBacterial Assays of compounds 2 to 10.

TABLE 1

AntiBacterial Assays of compounds 2 to 10

| Compound No. | MIC (μg/mL) |
| --- | --- |
| Huanamycin A | 8 μg/mL |
| 2 | >32 μg/mL |
| 3 | 16 μg/mL |
| 4 | 16 μg/mL |
| 5 | >32 μg/mL |
| 6 | >32 μg/mL |
| 7 | 16 μg/mL |
| 8 | >32 μg/mL |
| 9 | Not determined |
| 10 | 8 μg/mL |

EXAMPLES

Following examples are given by way of illustration therefore should not be construed to limit the scope of the invention.

Examples 1: Synthesis of Hunanamycin A

A: Synthesis of 6,7-dimethyl-1-((2S,3S,4R)-2,3,4,5-tetrahydroxypentyl)-1,4-dihydroquinoxaline-2,3-dione (2)

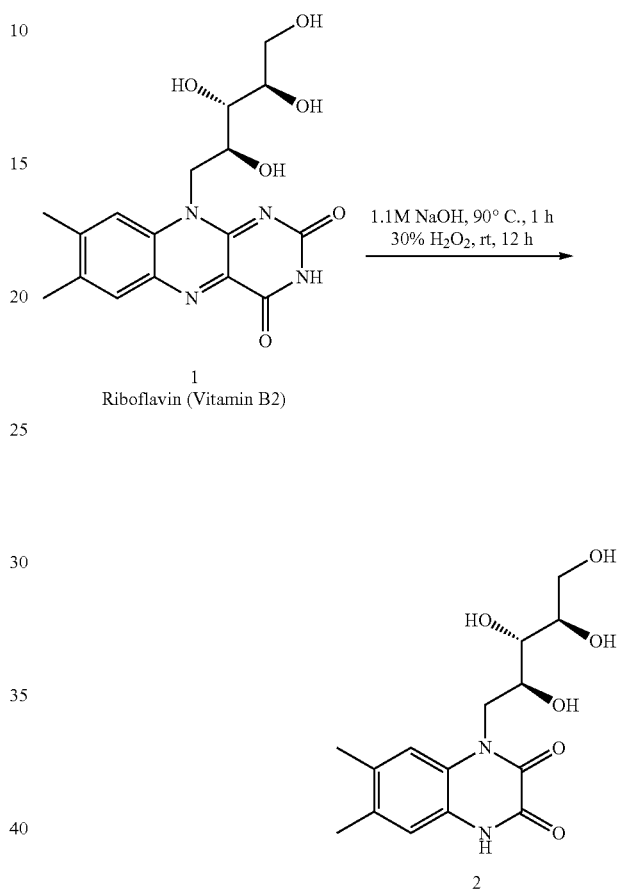

7,8-dimethyl-10-((2S,3S,4R)-2,3,4,5-tetrahydroxypentyl)benzo[g]pteridine-2,4(3H,10H)-dione (Riboflavin or Vitamin B2, 1) (6.0 g, 15.0 mmol) was dissolved in 1M NaOH (48 mL, 48.0 mmol) and heated at 90° C. for 1 h. The reaction mixture was then cooled to 0° C. and 30% aq. H2O2 (18 mL, 159 mmol) was added dropwise and allowed to warm to RT with additional 12 h of stirring. The solution was then neutralized with acetic acid (until pH=6) and allowed to stand for 12 h at 0° C. The bright yellow precipitate thus obtained was filtered, washed with minimum amount of water (40 mL) and dried under reduced pressure to afford 2 as yellow solid (4.3 g, 84%) $[\alpha]_{25}^{D}=-59$ (c 0.15, MeOH:H2O (1:1)); Melting point: 241-243° C.; $^1$H NMR (400 MHz, DMSO-$d_6$) □=11.84 (br. s., 1H), 7.31 (s, 1H), 6.91 (s, 1H), 4.92 (br. s., 1H), 4.78 (br. s., 1H), 4.62 (d, J=5.4 Hz, 1H), 4.46 (br. s., 2H), 4.15-3.92 (m, 2H), 3.50-3.62 (m, 3H) 3.44 (br. s., 1H), 2.21 (s, 3H), 2.18 (s, 3H); $^{13}$C NMR (100 MHz, DMSO-$d_6$) □=155.8, 153.8, 131.3, 131.0, 124.9, 123.4, 116.6, 116.0, 73.6, 72.7, 68.2, 63.5, 44.6, 19.3, 18.8; IR (Nujol) □/cm–$^1$: 3387, 2923, 2858, 1684, 1456, 1376, 1307; MS (ESI): m/z calculated for $C_{15}H_{20}N_2O_6$ [M+Na]$^+$ 347.12, found 347.1.

B: Synthesis of 6,7-dimethyl-1-(3-methylbut-2-en-1-yl)-4-((2S,3S,4R)-2,3,4,5-tetrahydroxy pentyl)-1,4-dihydroquinoxaline-2,3-dione (3)

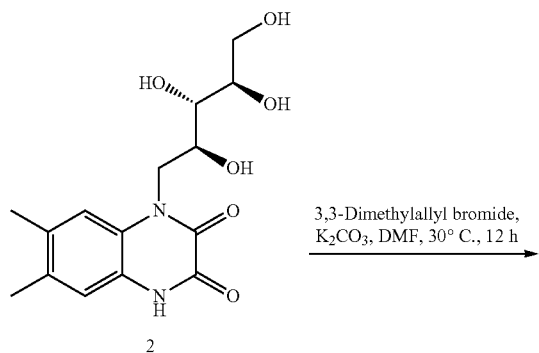

C: Synthesis of 7,7,8,9-tetramethyl-1-((2S,3S,4R)-2,3,4,5-tetrahydroxypentyl)-6,7-dihydro-1H,5H-4l4,4l5-4,41-methanopyrido[3,2,1-ij]quinoxaline-2,3-dione (Hunanamycin A)

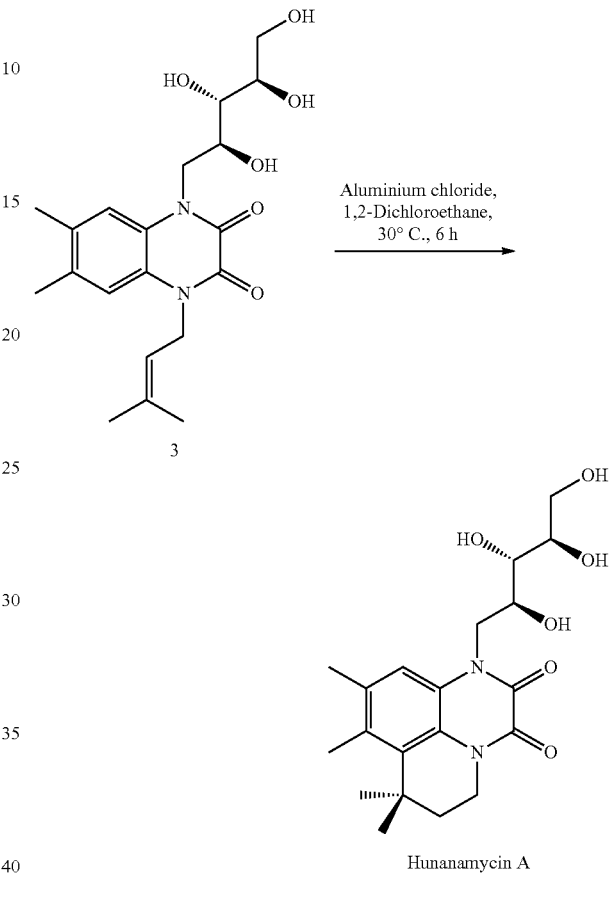

6,7-dimethyl-1-((2S,3S,4R)-2,3,4,5-tetrahydroxypentyl)-1,4-dihydroquinoxaline-2,3-dione (2) (2.0 g, 6.2 mmol) was dissolved in DMF (30 mL), and potassium carbonate (3.4 g, 24.6 mmol), 3,3-dimethylallyl bromide (1.44 mL, 13.5 mmol) were added sequentially at RT. The reaction mixture was stirred for 12 h at the room temperature. The excess DMF was then removed in vacuo, and cold water (30 mL) was added to obtain precipitate, which was filtered, washed with cold water (30 mL) and dried under reduced pressure. The crude residue obtained was again washed several times with 2% methanol in dichloromethane (5×20 mL) to afford 4 as pure white solid (1.99 g, 82%); Data for 3: [α]25D=+75 (c 0.2, MeOH); Melting point—180-183° C., $^1$H NMR (400 MHz, DMSO-d$_6$) □=7.40 (s, 1H), 7.06 (s, 1H), 5.13 (br. s., 1H), 4.94 (br. s., 1H), 4.80 (br. s., 1H), 4.74 (br. s., 3H), 4.67-4.50 (m, 3H), 4.46 (br. s., 1H), 4.15-3.94 (m, 3H), 3.57 (br. s., 3H), 3.43 (br. s., 1H), 2.24 (br. s., 6H), 1.85 (br. s., 3H), 1.69 (br. s., 3H); $^{13}$C NMR (100 MHz, DMSO-d$_6$) □=154.3, 153.5, 136.1, 131.6, 131.4, 125.0, 124.0, 118.6, 117.0, 115.9, 73.6, 72.8, 68.1, 63.5, 44.6, 40.6, 25.3, 19.1, 19.1, 18.2; IR (Nujol) □/cm–$^1$: 3351, 2855, 1676, 1456, 1375, 1310, 1197, 1032; MS (ESI): m/z calculated for $C_{20}H_{28}N_2O_6$ [M+1]$^+$ 393.3, found 393.3.

6,7-dimethyl-1-(3-methylbut-2-en-1-yl)-4-((2S,3S,4R)-2,3,4,5-tetrahydroxypentyl)-1,4-dihydroquinoxaline-2,3-dione (4) (3.7 g, 9 4 mmol) was taken in 1,2-dichloroethane (60 mL) and aluminum chloride (12.3 g, 94.4 mmol) was added portion wise and stirred for 6 h at RT. The reaction mixture was then added to crushed ice (~50 g), extracted with 10% methanol in dichloromethane (5×100 mL). The aqueous layer was extracted multiple times for the complete recovery of the product. The combined organic layer was then washed with brine, dried over anhydrous Na2SO4 and concentrated under reduced pressure to obtain crude product which was then triturated with diethyl ether (3×40 mL) to afford product as yellow solid (2.6 g, 70%) Data for Hunanamycin A: [α]=+13° (c 0.3, MeOH); Melting point: 154-157° C.; $^1$H NMR (400 MHz, METHANOL-d$_4$) □=7.45 (s, 1H), 4.77 (dd, J=10.3, 14.7 Hz, 1H), 4.28-4.16 (m, 2H), 4.16-4.04 (m, 2H), 3.84-3.70 (m, 3H), 3.70-3.62 (m, 1H), 2.46 (s, 3H), 2.34 (s, 3H), 1.94 (t, J=5.9 Hz, 2H), 1.54 (s, 6H); $^{13}$C NMR (100 MHz, METHANOL-d$_4$) □=156.6, 155.3, 136.0, 134.2, 133.7, 126.3, 123.4, 117.2, 75.0, 74.4, 70.9, 65.0, 46.6, 40.8, 39.3, 34.5, 29.4, 29.0, 21.6, 19.6; IR (CHCl$_3$) □/cm–$^1$: 3428, 2910, 2850, 1655, 1415, 1031; MS (ESI): m/z calculated for $C_{20}H_{28}N_2O_6$ [M+1]$^+$ 393.3, found 393.3.

Example 2: Synthesis of 1-allyl-6,7-dimethyl-4-((2S,3S,4R)-2,3,4,5-tetrahydroxypentyl)-1,4-dihydroquinoxaline-2,3-dione(4)

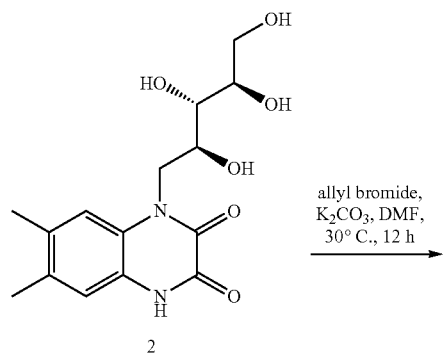

6,7-dimethyl-1-((2S,3S,4R)-2,3,4,5-tetrahydroxypentyl)-1,4-dihydroquinoxaline-2,3-dione (2) (0.2 g, 0.61 mmol) was dissolved in DMF (10 mL), potassium carbonate (0.25 g, 1.85 mmol) and allyl bromide (0.16 mL, 1.85 mmol) was added sequentially at 30° C. Reaction mixture was stirred for 12 h at same temperature. All the solvent was removed on vacuum, cold water was added and the white solid obtained was filtered and washed with minimum water and dried over rota vapour. This solid was again washed with DCM to afford the pure product (0.16 g, yield 72%) 1H NMR (400 MHz, DMSO-d6) Shift=7.41 (s., 1H), 7.09 (s., 1H), 5.92 (dt, J=5.4, 11.0 Hz, 1H), 5.23-5.10 (m, 3H), 4.76 (br. s., 2H), 4.67-4.48 (m, 3H), 4.14-3.98 (m, 3H), 3.61 (d, J=11.2 Hz, 2H), 3.43 (d, J=6.8 Hz, 2H), 2.23 (s., 6H).

Example 3: Synthesis of 1-ethyl-6,7-dimethyl-4-((2S,3S,4R)-2,3,4,5-tetrahydroxypentyl)-1,4-dihydroquinoxaline-2,3-dione (5)

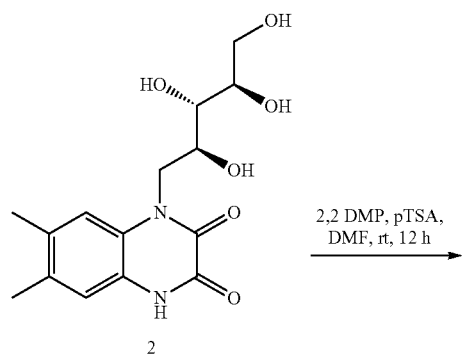

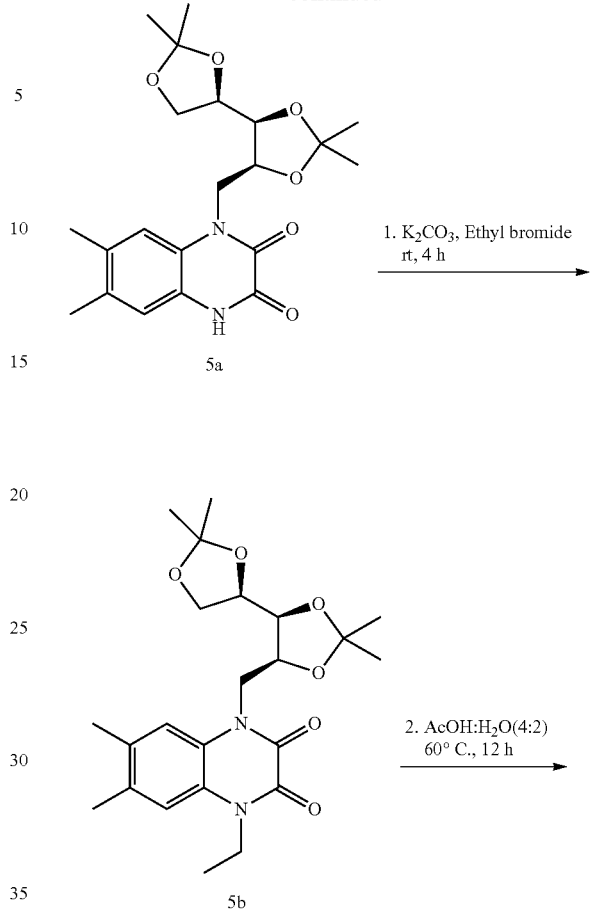

2-Methoxypropene (1.77 mL, 24.6 mmol) and p-Toluenesulfonic acid (117 mg, 6.1 mmol) were added in sequence to a stirred solution of the 6,7-dimethyl-1-((2S,3S,4R)-2,3,4,5-tetrahydroxypentyl)-1,4-dihydroquinoxaline-2,3-dione (2) (2 g, 6.17 mmol) in N,N-dimethylformamide (18 mL) at 24° C. The reaction mixture was stirred for 12 h at 24° C. The reaction mixture was treated with saturated aqueous sodium bicarbonate solution (10 mL) and extracted with ethyl acetate (20 mL×2). The organic layers were combined and dried over sodium sulfate. The dried solution was filtered and the filtrate was concentrated. The residue obtained was purified by flash-column chromatography (eluting with 15% ethyl acetate-dichloromethane) to afford the acetonide (5a) as a yellow solid (2.1 g, 83%).

$^1$H NMR (200 MHz, CHLOROFORM-d) □=11.86 (d, J=16.5 Hz, 1H), 7.23-7.04 (m, 2H), 4.71-4.46 (m, 2H), 4.42-3.92 (m, 3H), 3.87-3.58 (m, 2H), 2.30 (d, J=4.9 Hz, 6H), 1.65 (s, 1H), 1.59-1.23 (m, 12H).

6,7-dimethyl-1-(((4S,4'R,5S)-2,2,2',2'-tetramethyl-[4,4'-bi(1,3-dioxolan)]-5-yl)methyl)-1,4-dihydroquinoxaline-2,3-dione (200 mg, 0.49 mmol) (5a) was taken in dry DMF (5 mL) then potassium carbonate (102 mg, 0.74 mmol) and ethyl bromide (79 □L, 0.74 mmol) was added sequentially. Reaction mixture was stirred at room temperature for 12 h. The reaction mixture was then diluted with water (10 mL) and extracted with ethyl acetate (20 mL×2). The organic layers were combined and dried over sodium sulfate. The dried solution was filtered and the filtrate was concentrated. The residue obtained was purified by flash-column chromatography (eluting with 10% ethyl acetate-dichloromethane) to afford the N alkylated product as a yellow oil (135 mg, 62%).

The obtained product forwarded for next step without further characterization

A solution of 1-ethyl-6,7-dimethyl-4-(((4S,4'R,5S)-2,2,2',2'-tetramethyl-[4,4'-bi(1,3-dioxolan)]-5-yl)methyl)-1,4-dihydroquinoxaline-2,3-dione (5b) (100 mg, 0.231 mmol) in acetic acid:water (1:1 1 mL) was stirred for 12 h at 60° C. The reaction mixture was concentrated under reduced pressure, and purified by flash column chromatography (10% MeOH:CH$_2$Cl$_2$) to give compound 5 (58 mg, 71%) as colourless solid.

Data for 5: Specific rotation [α]=+5.6° (c 0.24, DMF); $^1$H NMR (400 MHz, DMSO-d$_6$) □=7.40 (s, 1H), 7.23 (s, 1H), 4.94 (br. s., 1H), 4.64 (d, J=5.9 Hz, 1H), 4.57 (dd, J=10.3, 13.2 Hz, 1H), 4.47 (t, J=5.1 Hz, 1H), 4.20-4.11 (m, 2H), 4.08 (br. s., 1H), 4.01 (d, J=14.2 Hz, 1H), 3.68-3.53 (m, 3H), 3.48-3.38 (m, 1H), 2.28 (s, 3H), 2.24 (s, 3H), 1.22 (t, J=6.8 Hz, 3H) $^{13}$C NMR (101 MHz, CHLOROFORM-d) □=154.3, 153.4, 131.8, 131.5, 125.0, 123.8, 117.1, 115.6, 73.6, 72.8, 68.1, 63.5, 44.6, 37.3, 19.1, 19.0, 12.2

Example 4: Synthesis of 1-(2-cyclohexylidene-ethyl)-6,7-dimethyl-4-((2S,3S,4R)-2,3,4,5-tetrahydroxypentyl)-1,4-dihydroquinoxaline-2,3-dione (6)

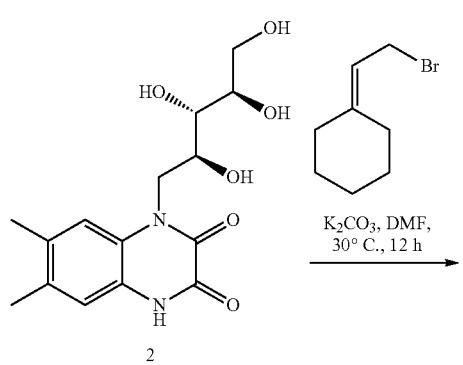

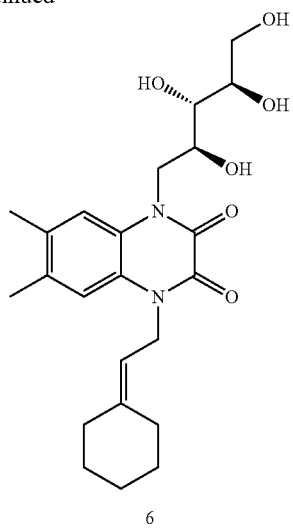

6,7-dimethyl-1-((2S,3S,4R)-2,3,4,5-tetrahydroxypentyl)-1,4-dihydroquinoxaline-2,3-dione (2) (0.5 g, 1.54 mmol) was dissolved in DMF (20 mL), potassium carbonate (0.320 g, 2.31 mmol) and (2-bromoethylidene)cyclohexane (0.435 g, 2.31 mmol) was added sequentially at 30° C. Reaction mixture was stirred for 12 h at same temperature. All the solvent was removed on vacuum, cold water was added and the white solid obtained was filtered and washed with minimum water and dried over rota vapour. This solid was again washed with DCM to afford the pure solid product (0.370 g, yield 55%)

Data for 6 Specific rotation [α]=−17 (c 0.2, DMF); $^1$H NMR (200 MHz, DMSO-d$_6$) □=7.41 (s, 1H), 7.07 (s, 1H), 5.01 (d, J=15.2 Hz, 2H), 4.82 (d, J=12.5 Hz, 2H), 4.65-4.53 (br. s., 3H), 4.05 (br. s., 3H), 3.58 (br. s., 4H), 2.40 (br. s., 2H), 2.33-2.18 (s, 6H), 2.05 (br. s., 2H), 1.58 (br. s., 6H); $^{13}$C NMR (101 MHz, CHLOROFORM-d) □=154.3, 153.6, 143.6, 131.6, 131.4, 131.4, 128.8, 128.7, 124.0, 117.1, 115.9, 115.4, 73.5, 72.9, 68.1, 63.5, 44.7, 36.2, 28.6, 27.9, 27.3, 26.1, 19.1

Example 5: Synthesis of ethyl 2-(6,7-dimethyl-2,3-dioxo-4-((2S,3S,4R)-2,3,4,5-tetrahydroxy pentyl)-3,4-dihydroquinoxalin-1(2H)-yl)acetate (7)

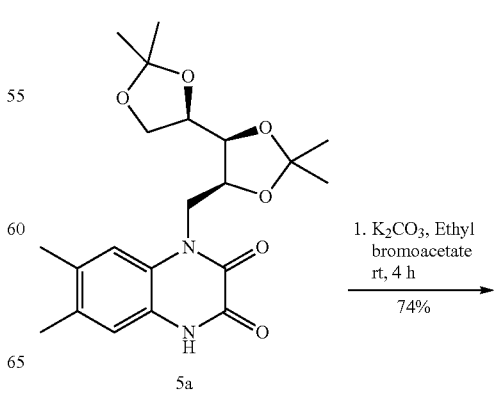

21
-continued

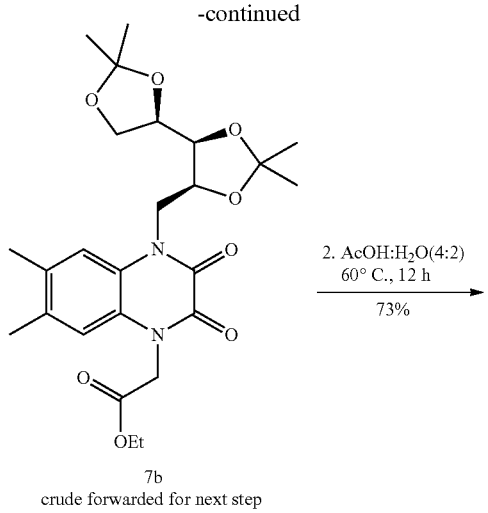

7b
crude forwarded for next step

→ 2. AcOH:H₂O(4:2) 60° C., 12 h
73%

[Structure of compound 7]

7

Experimental procedure followed was same as shown in example 3

Compound 7 obtained as white solid product (0.108 g, yield 73%) Data for compound 7: $^1$H NMR (400 MHz, DMSO-$d_6$) □=7.45 (s, 1H), 7.13 (s, 1H), 4.97 (s, 3H), 4.89-4.79 (m, 1H), 4.67 (d, J=6.4 Hz, 1H), 4.60 (dd, J=10.3, 13.2 Hz, 1H), 4.48 (t, J=5.4 Hz, 1H), 4.19 (q, J=6.8 Hz, 2H), 4.14-3.99 (m, 2H), 3.69-3.53 (m, 3H), 3.44 (dd, J=5.1, 10.5 Hz, 1H), 2.24 (br. s., 3H), 2.24 (br. s., 3H), 1.23 (t, J=7.1 Hz, 3H); $^{13}$C NMR (101 MHz, CHLOROFORM-d) □=167.6, 153.9, 132.0, 131.9, 124.7, 124.3, 117.1, 115.7, 73.6, 72.8, 68.1, 63.5, 61.3, 44.7, 44.4, 19.1, 18.9, 14.0

22

Example 6: 1-benzyl-6,7-dimethyl-4-((2S,3S,4R)-2,3,4,5-tetrahydroxypentyl)-1,4-dihydro quinoxaline-2,3-dione (8)

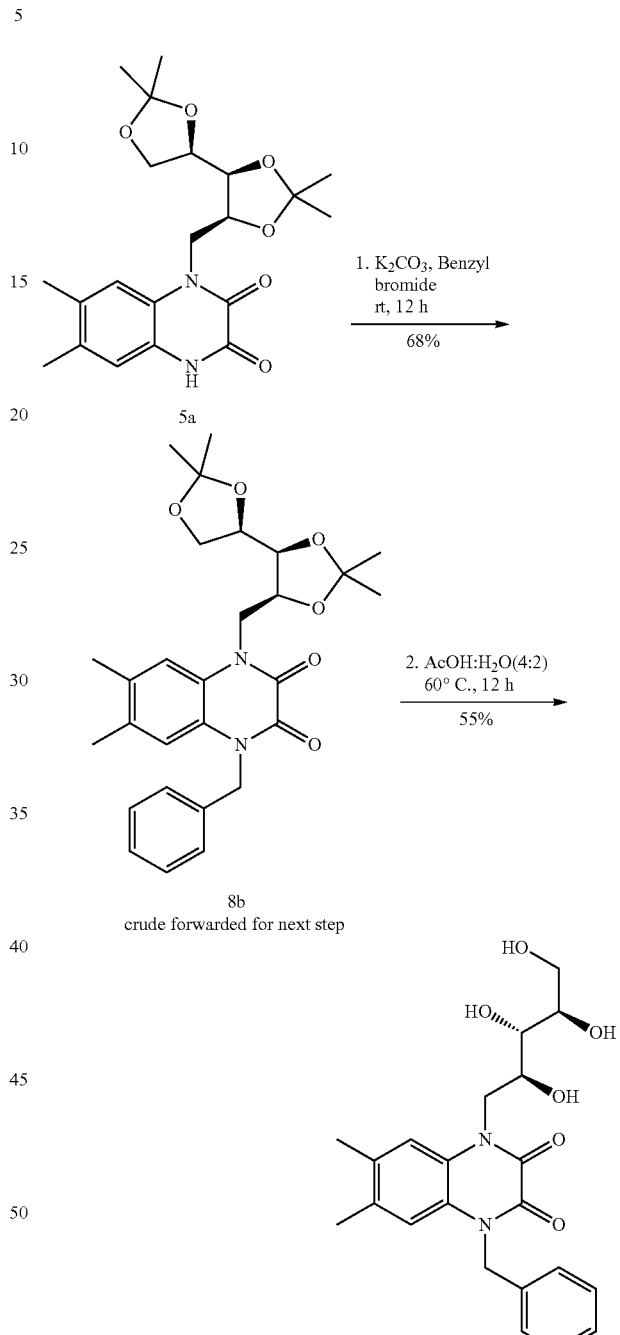

Experimental procedure followed was same as shown in example 3

Compound 8 obtained as white solid product (38 mg, yield 55%) Data for compound 8: $^1$H NMR (400 MHz, DMSO-$d_6$) □=7.38 (s, 1H), 7.35-7.20 (m, 5H), 7.05 (s, 1H), 5.39 (br. s., 2H), 5.19 (dd, J=5.6, 15.4 Hz, 2H), 4.88 (d, J=5.4 Hz, 1H), 4.55 (dd, J=10.5, 13.9 Hz, 1H), 4.26-4.17 (m, 1H), 4.11 (d, J=12.7 Hz, 2H), 4.03 (dd, J=6.8, 11.2 Hz, 1H), 3.83 (d, J=4.9 Hz, 1H), 3.65-3.56 (m, 1H), 2.21 (s, 3H), 2.13 (s, 3H); $^{13}$C NMR (101 MHz, CHLOROFORM-d) δ=154.3, 154.3, 135.9, 131.7, 131.4, 128.6, 127.2, 126.7, 125.2, 124.2, 117.0, 116.3, 73.6, 69.7, 67.8, 66.3, 45.6, 45.1, 19.1, 19.0

Example 7: Synthesis of 1-isopentyl-6,7-dimethyl-4-((2S,3S,4R)-2,3,4,5-tetrahydroxypentyl)-1,4-dihydroquinoxaline-2,3-dione (9)

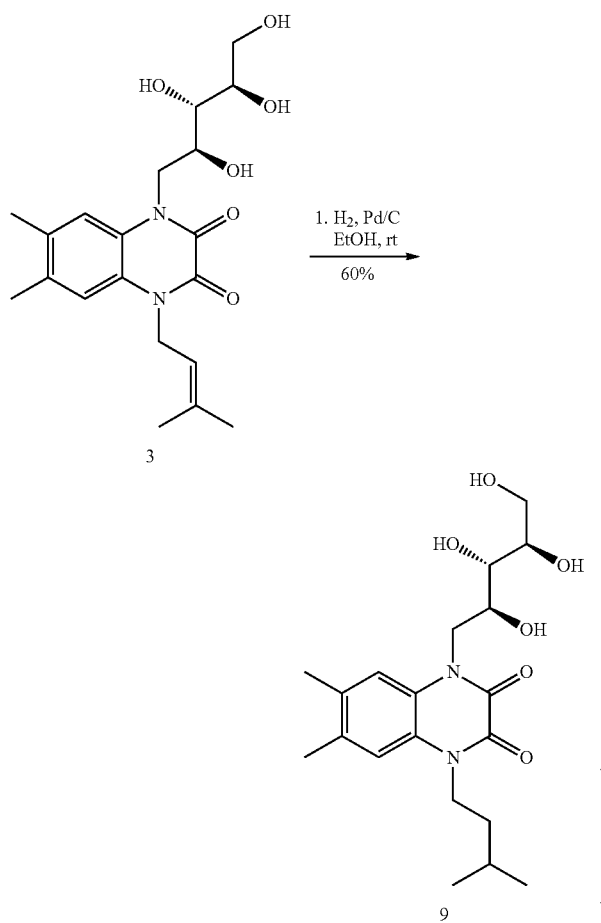

6,7-dimethyl-1-(3-methylbut-2-en-1-yl)-4-((2S,3S,4R)-2,3,4,5-tetrahydroxypentyl)-1,4-dihydroquinoxaline-2,3-dione (3)(200 mg, 0.51 mmol) was taken in ethanol (10 mL) and 10% Pd/C (20 mg) was added. Stirred reaction mixture at room temperature for 12 h. Filter the reaction mixture through celite pad wash with more ethanol (30 mL). Filtrate was then concentrate to obtain crude product which was then washed with 1:1 mixture of DCM:petether to obtain pure compound 9 as white solid product (120 mg, yield 60%).

Data for 9: Specific rotation [α]=+137 (c 0.2, DMF); $^1$H NMR (400 MHz, DMSO-d$_6$) δ=7.42 (br. s., 1H), 7.13 (br. s., 1H), 5.11 (br. s., 1H), 4.99 (br. s., 1H), 4.73 (br. s., 1H), 4.68-4.47 (m, 2H), 4.32-4.07 (m, 2H), 4.02 (d, J=14.2 Hz, 2H), 3.62 (br. s., 1H), 3.57 (br. s., 2H), 3.45 (br. s., 1H), 2.27 (br. s., 3H), 2.24 (br. s., 3H), 1.69 (d, J=5.9 Hz, 1H), 1.56-1.42 (m, 2H), 0.97 (d, J=5.9 Hz, 6H); $^{13}$C NMR (101 MHz, CHLOROFORM-d) δ=154.2, 153.6, 131.7, 131.6, 125.0, 123.9, 117.2, 115.6, 73.6, 72.9, 68.1, 63.5, 44.7, 40.6, 35.4, 25.7, 22.4, 19.1

Example 8: Synthesis of 1-(2-cyclohexylethyl)-6,7-dimethyl-4-((2S,3S,4R)-2,3,4,5-tetrahydroxypentyl)-1,4-dihydroquinoxaline-2,3-dione (10)

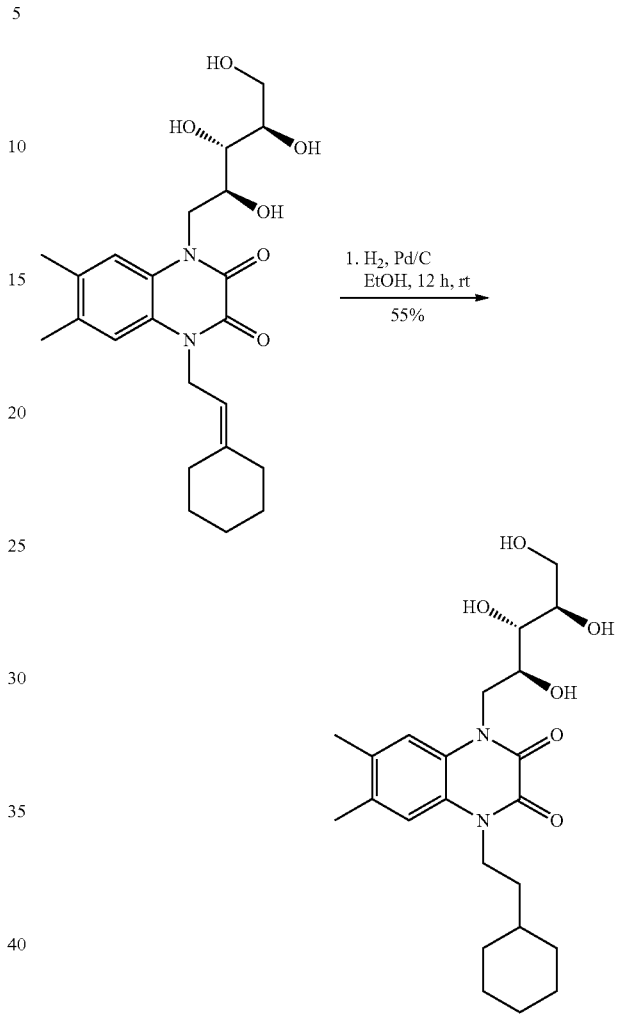

Experimental procedure followed was same as shown in example 7

Compound 10 obtained as white solid product (56 mg, yield 55%) Data for 10: Specific rotation [α]=−15 (c 0.22, DMF); $^1$H NMR (400 MHz, DMSO-d$_6$) δ$^1$H NMR (400 MHz, DMSO-d$_6$) δ=7.41 (s, 1H), 7.13 (s, 1H), 4.95 (br. s., 1H), 4.82 (br. s., 1H), 4.64 (d, J=5.4 Hz, 1H), 4.62-4.52 (m, 1H), 4.47 (t, J=5.1 Hz, 1H), 4.18-4.07 (m, 4H), 4.02 (d, J=14.2 Hz, 1H), 3.66-3.51 (m, 3H), 3.48-3.37 (m, 1H), 2.27 (s, 3H), 2.24 (s, 3H), 1.80 (d, J=11.7 Hz, 2H), 1.76-1.58 (m, 3H), 1.56-1.44 (m, 2H), 1.40 (br. s., 1H), 1.31-1.11 (m, 3H), 1.07-0.89 (m, 2H); $^{13}$C NMR (101 MHz, CHLOROFORM-d) δ=154.2, 153.5, 131.7, 131.5, 125.0, 123.9, 117.1, 115.6, 73.6, 72.8, 68.0, 63.5, 44.6, 35.0, 33.9, 32.6, 26.0, 25.7, 19.1.

Example 9: Antibacterial Activity Assays of Compounds 2 to 10

The minimum inhibitory concentrations (MICs) were determined using the Promega Bac Titer-Glo microbial cell viability assay, which measures cell viability by quantitation of ATP present, an indicator of metabolic activity of cells. The assays were carried out using *Salmonella enterica* strain AMC (ATCC #6539), Inocula of *S. enterica* were prepared from 12-h broth cultures grown in Mueller Hinton broth and the suspensions were then adjusted to a turbidity of 0.5 McFarland. Assays were conducted in a 96-well plate using growth media with an inoculum of ~5~$10^4$ CFU/mL using the suggested protocols. Bacterial cells were treated with hunanamycin analogs for 24 hours at ranges from 0.4 to 40 μg/mL and ciprofloxacin as a control ranging from 0.03 to 10 μg/mL. The $OD_{600}$ was measured using an Envision multimodal plate reader (Perkin-Elmer, Inc.). The antibiotic assays were performed in Prof. John B. MacMillan's lab, Department of Biochemistry, University of Texas Southwestern Medical Center at Dallas, USA.

TABLE 1

Antibacterial Assays of compounds 2 to 10

| Compound No. | MIC (μg/mL) |
| --- | --- |
| Huanamycin A | 8 μg/mL |
| 2 | >32 μg/mL |
| 3 | 16 μg/mL |
| 4 | 16 μg/mL |
| 5 | >32 μg/mL |
| 6 | >32 μg/mL |
| 7 | 16 μg/mL |
| 8 | >32 μg/mL |
| 9 | Not determined |
| 10 | 8 μg/mL |

Advantages of the Invention

Compound of formula (I) provided having antibacterial activity
Hunanamycin A and compounds of formula (I) and (II) obtained in high yields
Cheap Starting material (Riboflavin)
Short synthesis (three steps)
Protecting group free synthesis
Achieved gram scale biomimetic synthesis of Hunanamycin A using cheap starting material, no column purification in step economy fashion.
Synthesis of Hunanamycin A using cheap starting material, no column purification in step economy fashion. Current method is far superior than the reported methods.

We claim:

1. A cyclic compound of formula (I) or a pharmaceutically acceptable salt thereof;

Formula (I)

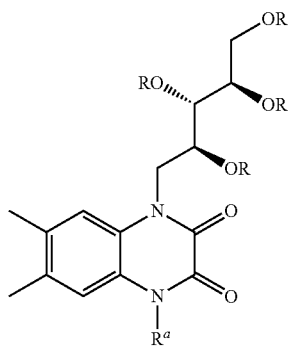

wherein R is selected from hydrogen, alkyl, aralkyl, alkoxyalkyl;
two R groups may be cyclized to form 5 or 6 membered ring which further substituted with alkyl groups or oxo group;
wherein $R^a$ is selected from sugar, sugar mimic, alkyl, aryl, aralkyl, alkenyl, alkynyl, haloalkyl, hydroxyalkyl, alkoxyalkyl, aminoalkyl, —$CH_2NR'R''$—$CONR'R''$,—$COOR'''$;
wherein R', R", R'" are independently hydrogen or alkyl, aryl, aralkyl which have additional substitution.

2. The compound as claimed in claim 1, wherein said compound is selected from group consisting of 6,7-dimethyl-1-(3-methylbut-2-en-1-yl)-4-((2S,3S,4R)-2,3,4,5-tetrahydroxypentyl)-1,4-dihydroquinoxaline-2,3-dione (3);
1-allyl-6,7-dimethyl-4-((2S,3S,4R)-2,3,4,5-tetrahydroxypentyl)-1,4-dihydroquinoxaline-2,3-dione (4);
1-ethyl-6,7-dimethyl-4-((2S,3S,4R)-2,3,4,5-tetrahydroxypentyl)-1,4-dihydroquinoxaline-2,3-dione (5);
1-(2-cyclohexylideneethyl)-6,7-dimethyl-4-((2S,3S,4R)-2,3,4,5-tetrahydroxypentyl)-1,4-dihydroquinoxaline-2,3-dione (6);
Ethyl-2-(6,7-dimethyl-2,3-dioxo-4-((2S,3S,4R)-2,3,4,5-tetrahydroxypentyl)-3,4-dihydroquinoxalin-1(2H)-yl) acetate (7);
1-benzyl-6,7-dimethyl-4-((2S,3S,4R)-2,3,4,5-tetrahydroxypentyl)-1,4-dihydroquinoxaline-2,3-dione (8);
1-isopentyl-6,7-dimethyl-4-((2S,3S,4R)-2,3,4,5-tetrahydroxypentyl)-1,4-dihydroquinoxaline-2,3-dione (9);
1-(2-cyclohexylethyl)-6,7-dimethyl-4-((2S,3S,4R)-2,3,4,5-tetrahydroxypentyl)-1,4-dihydroquinoxaline-2,3-dione (10).

3. A process for the preparation of compound of formula (I) as claimed in claim 1, wherein said process comprising the steps of:
a) heating the basic solution of Riboflavin at temperature ranging from 80 to 90° C. for the time period ranging from 1 to 2 h followed by adding suitable oxidizing agent and stirring resultant mixture at the temperature ranging from 25 to 30° C. for the time period ranging from 10 to 12 hrs to afford dione compound (2);
b) stirring the reaction mixture of compound of step (a), base and suitable alkylating agent in solvent at the temperature ranging from 25 to 30° C. for the time period ranging from 10 to 12 hrs to obtain compound of formula (I).

4. The process as claimed in claim 3, wherein said base in step (b) is selected from the group consisting of sodium hydroxide, potassium hydroxide, potassium carbonate, cesium carbonate or sodium carbonate.

5. The process as claimed in claim 3, wherein said solvent of step (b) is selected from the group consisting of dimethylformamide, N-methylpyrrolidine or dimethyl sulphoxide.

6. The process as claimed in claim 3, wherein said alkylating agent in step (b) is selected from the group consisting of 3,3-Dimethylallyl bromide or 3,3-Dimethylallyl chloride.

7. The process as claimed in claim 3, wherein said oxidizing agent in step (a) is hydrogen peroxide.

8. A process for the conversion of the compound of formula (I) according to claim 1 into Formula (II), the process comprising:
adding Lewis acid to a solution of compound of formula (I) wherein $R^a$ is alkenyl, in solvent at temperature ranging from 25 to 30° C.

stirring the reaction mixture at temperature ranging from 25 to 30° C. for the time period ranging from 5 to 6 hours to obtain compound of formula (II):

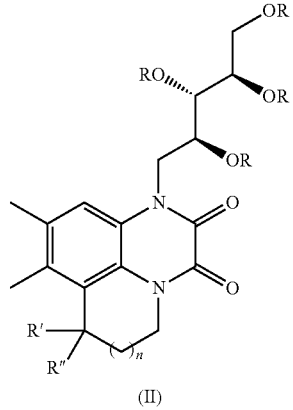

Formula (II)

(II)

wherein R is selected from hydrogen, alkyl, aralkyl, alkoxyalkyl;

two R groups may be cyclized to form 5 or 6 membered ring which may further substituted with alkyl groups or oxo group;

wherein R', R", are independently hydrogen or alkyl, aryl, aralkyl which may have additional substitution;

n is 0, 1, 2, or 3.

9. The process as claimed in claim 8, wherein said Lewis acid is selected from the group consisting of aluminium chloride ($AlCl_3$).

10. The process as claimed in claim 8, wherein said compound of formula (II) is Hunanamycin A, wherein the alkyenyl is 3,3-dimethylallyl.

11. A pharmaceutical composition comprising novel cyclic compound of formula (I) as recited in claim 1

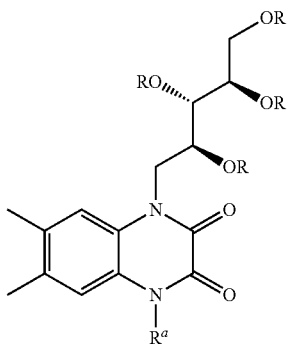

(I)

or or a stereoisomer, or ester or pharmaceutically acceptable salt thereof and at least one pharmaceutically acceptable carrier.

12. A method for treating bacterial infection caused by gram negative bacteria in a subject in need thereof; comprising administering to the said subject a therapeutically effective amount of the compound of formula (I) as recited in claim 1

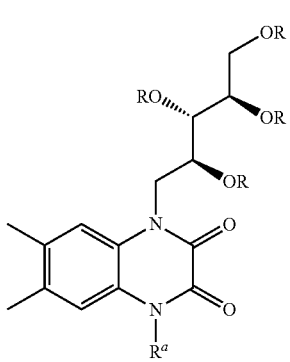

(I)

or a pharmaceutically acceptable salt thereof.

* * * * *